(12) United States Patent
Wenderow et al.

(10) Patent No.: US 12,150,796 B2
(45) Date of Patent: *Nov. 26, 2024

(54) SYSTEM AND METHOD FOR CONTROLLING X-RAY FRAME RATE OF AN IMAGING SYSTEM

(71) Applicant: Corindus, Inc., Waltham, MA (US)

(72) Inventors: Tal Wenderow, Newton, MA (US); David Handler, Newton, MA (US); Nicholas Kottenstette, Sterling, MA (US)

(73) Assignee: Corindus, Inc., Newton, MA (US)

( * ) Notice: Subject to any disclaimer, the term of this patent is extended or adjusted under 35 U.S.C. 154(b) by 17 days.

This patent is subject to a terminal disclaimer.

(21) Appl. No.: 17/654,840

(22) Filed: Mar. 15, 2022

(65) Prior Publication Data

US 2022/0202381 A1 Jun. 30, 2022

Related U.S. Application Data

(63) Continuation of application No. 16/062,305, filed as application No. PCT/US2016/066362 on Dec. 13, 2016, now Pat. No. 11,304,668.

(Continued)

(51) Int. Cl.
*A61B 6/12* (2006.01)
*A61B 6/00* (2024.01)
(Continued)

(52) U.S. Cl.
CPC ............... *A61B 6/12* (2013.01); *A61B 6/405* (2013.01); *A61B 6/465* (2013.01); *A61B 6/466* (2013.01);
(Continued)

(58) Field of Classification Search
CPC ........... A61B 6/12; A61B 6/405; A61B 6/465; A61B 6/466; A61B 6/487; A61B 6/503;
(Continued)

(56) References Cited

U.S. PATENT DOCUMENTS

| 5,492,131 A | 2/1996 | Galel |
| 11,304,668 B2 * | 4/2022 | Wenderow ............ G16H 30/20 |

(Continued)

FOREIGN PATENT DOCUMENTS

| CN | 1672642 | 9/2005 |
| CN | 1894594 | 12/2007 |

(Continued)

OTHER PUBLICATIONS

Extended European Search Report for EP 16876482.7, mail date Jul. 15, 2019; 7 pages.

(Continued)

*Primary Examiner* — Sean D Mattson

(57) ABSTRACT

A method for controlling x-ray frame rate of an imaging system for a catheter procedure system includes generating a first control signal that indicates a first frame rate and providing the first control signal to an imaging system. The imaging system obtains a first set of images at the first frame rate based on the first control signal. At least one parameter of a catheter procedure performed by the catheter procedure system is determined and a second control signal is generated based on the at least one parameter of the catheter procedure. The second control signal indicates a second frame rate. The second control signal is provides to the imaging system to adjust the first frame rate to the second frame rate. The imaging system obtains a second set of images at the second frame rate and displays the second set of images on a display.

22 Claims, 5 Drawing Sheets

Related U.S. Application Data

(60) Provisional application No. 62/267,692, filed on Dec. 15, 2015.

(51) Int. Cl.

| | | |
|---|---|---|
| *A61B 6/40* | (2024.01) | |
| *A61B 6/46* | (2024.01) | |
| *A61B 6/50* | (2024.01) | |
| *A61B 34/20* | (2016.01) | |
| *A61M 5/00* | (2006.01) | |
| *G16H 20/40* | (2018.01) | |
| *G16H 30/20* | (2018.01) | |
| *G16H 30/40* | (2018.01) | |
| *G16H 40/63* | (2018.01) | |
| *A61B 34/30* | (2016.01) | |
| *A61B 90/00* | (2016.01) | |

(52) U.S. Cl.
CPC .............. *A61B 6/487* (2013.01); *A61B 6/503* (2013.01); *A61B 6/504* (2013.01); *A61B 6/542* (2013.01); *A61B 6/545* (2013.01); *A61B 34/20* (2016.02); *A61M 5/007* (2013.01); *G16H 20/40* (2018.01); *G16H 30/20* (2018.01); *G16H 30/40* (2018.01); *G16H 40/63* (2018.01); *A61B 2034/301* (2016.02); *A61B 2090/376* (2016.02)

(58) Field of Classification Search
CPC ......... A61B 6/504; A61B 6/542; A61B 6/545; A61B 6/486; A61B 34/20; A61B 2034/301; A61B 2090/376; A61M 5/007; A61M 5/00; G16H 20/40; G16H 30/20; G16H 30/40; G16H 40/63
See application file for complete search history.

(56) References Cited

U.S. PATENT DOCUMENTS

| | | |
|---|---|---|
| 2001/0025142 A1 | 5/2001 | Wessels et al. |
| 2004/0044279 A1 | 3/2004 | Lewin et al. |
| 2005/0238140 A1 | 10/2005 | Hardesty |
| 2006/0041181 A1 | 2/2006 | Viswanathan et al. |
| 2008/0287783 A1 | 11/2008 | Anderson |
| 2009/0105639 A1 | 4/2009 | Weitzner et al. |
| 2009/0137952 A1 | 5/2009 | Ramamurthy et al. |
| 2009/0221958 A1 | 9/2009 | Beyar et al. |
| 2010/0172556 A1 | 7/2010 | Cohen et al. |
| 2010/0324413 A1 | 12/2010 | Tetsuka et al. |
| 2011/0026676 A1* | 2/2011 | Takekoshi ............ G09G 5/005 378/98.2 |
| 2011/0170662 A1* | 7/2011 | Baumgart ............ A61B 6/504 378/62 |
| 2011/0319752 A1* | 12/2011 | Steinberg ............ A61B 6/541 600/424 |
| 2012/0250973 A1 | 10/2012 | Nambu |
| 2013/0216025 A1* | 8/2013 | Chan .................... A61B 6/54 378/63 |
| 2013/0231631 A1 | 9/2013 | Murphy et al. |
| 2015/0005620 A1 | 1/2015 | Bergman et al. |
| 2015/0139394 A1 | 5/2015 | Kang et al. |
| 2016/0029981 A1* | 2/2016 | Van Dijk ............... A61B 6/54 600/424 |

FOREIGN PATENT DOCUMENTS

| | | |
|---|---|---|
| CN | 101568296 | 10/2009 |
| CN | 102612338 | 7/2012 |
| CN | 103946717 | 7/2014 |
| CN | 104644197 | 5/2015 |
| DE | 10109586 | 9/2002 |
| EP | 2160978 | 3/2010 |
| IN | 101444424 | 6/2009 |
| JP | H9270955 | 10/1997 |
| JP | 2003284716 | 10/2003 |
| JP | 2012223500 | 11/2012 |
| WO | 2012056386 | 5/2012 |
| WO | 2012129374 | 9/2012 |
| WO | 2014162275 | 10/2014 |

OTHER PUBLICATIONS

European Search Report issued for Corresponding Appln No. 20195773.5, dated Dec. 17, 2020.

Hagelberg, Melker; Minimization of radiation dose exposure during PCI procedure; KTH Royal Institute of Technology; 2016, 63 pages.

Olcay, et al; Comparison of Fluoro and Cine Coronoary Angiography, Balancing Acceptable Outcomes with a Reduction in Radiation Dose; www.medscape.com; J Invasive Cardiol. 2015; 27(4); 199-202; 7 pages.

Sadamatsu, et al. The effect of low rate fluoroscopy on the X-ray Dose during Coronary Intervention; Internal Medicine; 2016; vol. 55; pp. 1943-1946; 4 pages.

\* cited by examiner

SYSTEM AND METHOD FOR CONTROLLING X-RAY FRAME RATE OF AN IMAGING SYSTEM

CROSS REFERENCE TO RELATED APPLICATIONS

The present application is a continuation of U.S. Application Ser. No. 16/062,305, filed Jun. 14, 2018, which is a U.S. National Phase Application of PCT/US2016/066362, filed Dec. 13, 2016, which claims the benefit of U.S. Provisional Application No. 62/267,692, filed Dec. 15, 2015, which is herein incorporated by reference in its entirety.

FIELD OF THE INVENTION

The present invention relates generally to robotic catheter procedure systems and, in particular, to a system and method for controlling x-ray frame rate of an imaging system for a catheter procedure system.

BACKGROUND OF THE INVENTION

Catheters may be used for many medical procedures, including inserting a guide wire, delivering a stent and delivering and inflating a balloon. Catheterization procedures are commonly performed for diagnosis and treatment of diseases of the heart and vascular systems. The catheterization procedure is generally initiated by inserting a guide wire into a blood vessel in the patient's body. The guide wire is then advanced to the desired location, most commonly in one of the heart vessels or elsewhere in the vascular system. At this point, a catheter is slid over the guide wire into the blood vessel and/or heart. In some procedures, the catheter is a balloon catheter or stent delivery system that when deployed at the site of the lesion allows for increased blood flow through the portion of the coronary artery that is affected by the lesion.

Robotic catheter procedure systems have been developed that may be used to aid a physician in performing a catheterization procedure such as a percutaneous coronary intervention (PCI). The physician uses a robotic system to precisely steer a coronary guide wire, balloon catheter or stent delivery system in order to, for example, widen an obstructed artery. In order to perform PCI, the distal tip of a guide wire must be navigated through coronary anatomy past a target lesion. While observing the coronary anatomy using fluoroscopy, the physician manipulates the proximal end of the guide wire in order to direct the distal tip into the appropriate vessels toward the lesion and avoid advancing into side branches. A fluoroscopy imaging system uses x-rays to obtain real-time images of the human vasculature and percutaneous devices within the vasculature. The frequency of images taken, or the frame rate (e.g., frames per second) effects the amount of radiation exposure or radiation dose for the patient and the medical professionals performing the catheter procedure. The frame rate can also affect the quality of the image acquired by the fluoroscopy system.

It would be desirable to provide a system and method for controlling x-ray frame rate of an imaging system for a catheter procedure system to reduce the number of x-ray images taken to reduce the x-ray exposure and also to provide appropriate quality of images to perform the catheter procedure.

SUMMARY OF THE INVENTION

In accordance with an embodiment, a method for controlling x-ray frame rate of an imaging system for a catheter procedure system, includes generating a first control signal that indicates a first frame rate, providing the first control signal to an imaging system, obtaining a first set of images at the first frame rate, determining at least one parameter of a catheter procedure performed by the catheter procedure system, generating a second control signal based on the at least one parameter of the catheter procedure, the second control signal indicating second frame rate, providing the second control signal to the imaging system to adjust the first frame rate to the second frame rate, obtaining a second set of images at the second frame rate and displaying the second set of images on a display.

In accordance with another embodiment, a catheter procedure system includes a bedside system having at least one percutaneous device and at least one drive mechanism coupled to the at least one percutaneous device, an imaging system; and a workstation coupled to the bed side system and the imaging system, the workstation having a user interface, at least one display, a controller coupled to the bedside system, the user interface, the at least one display and the imaging system, the controller programmed to generate a first control signal that indicates a first frame rate, provide the first control signal to the imaging system, determine at least one parameter of a catheter procedure performed by the catheter procedure system, generate a second control signal based on the at least one parameter of the catheter procedure, the second control signal indicating second frame rate and provide the second control signal to the imaging system to adjust the first frame rate to the second frame rate, wherein the imaging system is configured to obtain a first set of images at the first fame rate and to obtain a second set of images at the second frame rate.

BRIEF DESCRIPTION OF THE DRAWINGS

This application will become more fully understood from the following detailed description, taken in conjunction with the accompanying figures, wherein like reference numerals refer to like elements in which.

DETAILED DESCRIPTION OF THE PREFERRED EMBODIMENTS

Figure 1:
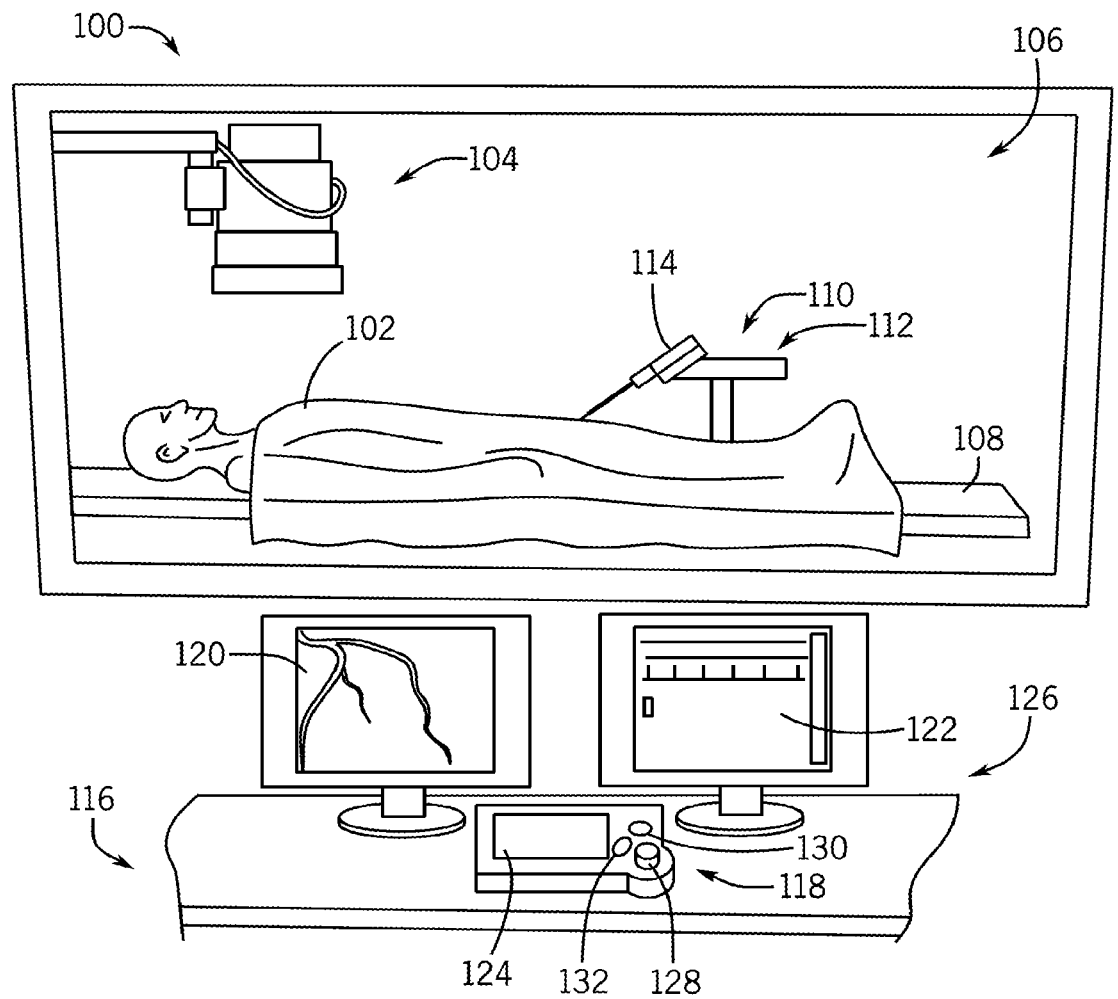
FIG. 1 is a perspective view of an exemplary catheter procedure system in accordance with an embodiment.

FIG. 1 is a perspective view of an exemplary catheter procedure system in accordance with an embodiment. In FIG. 1, a catheter procedure system 100 may be used to perform catheter based medical procedures (e.g., a percutaneous intervention procedure). Catheter based medical procedures may include diagnostic catheterization procedures during which one or more catheters are used to aid in the diagnosis of a patient's disease. For example, during one embodiment of a catheter based diagnostic procedure, a contrast media is injected onto one or more coronary arteries through a catheter and an image of the patient's heart is taken. Catheter based medical procedures may also include catheter based therapeutic procedures (e.g., angioplasty, stent placement, treatment of peripheral vascular disease, etc.) during which a catheter is used to treat a disease. It should be noted, however, that one skilled in the art would recognize that certain specific percutaneous intervention devices or components (e.g., type of guide wire, type of catheter, etc.) will be selected based on the type of procedure that is to be performed. Catheter procedure system 100 is capable of performing any number of catheter based medical procedures with minor adjustments to accommodate the specific percutaneous intervention devices to be used in the procedure. In particular, while the embodiments of catheter procedure system 100 describe herein are explained primarily in relation to the treatment of coronary disease, catheter procedure system 100 may be used to diagnose and/or treat any type of disease or condition amenable to diagnosis and/or treatment via a catheter based procedure.

Catheter procedure system 100 includes lab unit 106 and workstation 116. Catheter procedure system 100 includes a robotic catheter system, shown as bedside system 110, located within lab unit 106 adjacent a patient 102. Patient 102 is supported on a table 108. Generally, bedside system 110 may be equipped with the appropriate percutaneous intervention devices or other components (e.g., guide wires, guide catheters, working catheters such as balloon catheters and stent delivery systems, contrast media, medicine, diagnostic catheters, etc.) to allow the user to perform a catheter based medical procedure via a robotic system by operating various controls such as the controls located at workstation 116. Bedside system 110 may include any number and/or combination of components to provide bedside system 110 with the functionality described herein. Bedside system 110 includes, among other elements, a drive assembly 114 (e.g., that may contain a sterile, disposable portion) supported by a robotic arm 112 which may be used to automatically advance a guide wire into a guide catheter seated in an artery of the patient 102.

Bedside system 110 is in communication with workstation 116, allowing signals generated by the user inputs of workstation 116 to be transmitted to bedside system 110 to control the various functions of bedside system 110. Bedside system 110 may also provide feedback signals (e.g., operating conditions, warning signals, error codes, etc.) to workstation 116. Bedside system 110 may be connected to workstation 116 via a communication link 140 (shown in FIG. 2) that may be a wireless connection, cable connections, or any other means capable of allowing communication to occur between workstation 116 and bedside system 110.

Workstation 116 includes a user interface 126 configured to receive user inputs to operate various components or systems of catheter procedure system 100. User interface 126 includes controls 118 that allow the user to control bedside system 110 to perform a catheter based medical procedure. For example, controls 118 may be configured to cause bedside system 110 to perform various tasks using the various percutaneous intervention devices with which bedside system 110 may be equipped (e.g., to advance, retract, or rotate a guide wire, advance, retract or rotate a working catheter, advance, retract, or rotate a guide catheter, inflate or deflate a balloon located on a catheter, position and/or deploy a stent, inject contrast media into a catheter, inject medicine into a catheter, or to perform any other function that may be performed as part of a catheter based medical procedure). Drive assembly 114 includes various drive mechanisms to cause movement (e.g., axial and rotational movement) of the components of the bedside system 110 including the percutaneous devices.

In one embodiment, controls 118 include a touch screen 124, one or more joysticks 128 and buttons 130, 132. The joystick 128 may be configured to advance, retract, or rotate various components and percutaneous devices such as, for example, a guide wire, a guide catheter or a working catheter. Buttons 130, 132 may include, for example, an emergency stop button and a multiplier button. When an emergency stop button is pushed a relay is triggered to cut the power supply to bedside system 110. Multiplier button acts to increase or decrease the speed at which the associated component is moved in response to a manipulation of controls 118. In one embodiment, controls 118 may include one or more controls or icons (not shown) displayed on touch screen 124, that, when activated, causes operation of a component of the catheter procedure system 100. Controls 118 may also include a balloon or stent control that is configured to inflate or deflate a balloon and/or a stent. Each of the controls may include one or more buttons, joysticks, touch screen, etc. that may be desirable to control the particular component to which the control is dedicated. In addition, touch screen 124 may display one or more icons (not shown) related to various portions of controls 118 or to various components of catheter procedure system 100.

User interface 126 may include a first monitor or display 120 and a second monitor or display 122. First monitor 120 and second monitor 122 may be configured to display information or patient specific data to the user located at workstation 116. For example, first monitor 120 and second monitor 122 may be configured to display image data (e.g., x-ray images, MRI images, CT images, ultrasound images, etc.), hemodynamic data (e.g., blood pressure, heart rate, etc.), patient record information (e.g., medical history, age, weight, etc.). In addition, first monitor 120 and second monitor 122 may be configured to display procedure specific information (e.g., duration of procedure, catheter or guide wire position, volume of medicine or contrast agent delivered, etc.). Monitor 120 and monitor 122 may be configured to display information regarding the position the guide catheter. Further, monitor 120 and monitor 122 may be configured to display information to provide the functionalities associated with controller 134 (shown in FIG. 2) discussed below. In another embodiment, user interface 126 includes a single screen of sufficient size to display one or more of the display components and/or touch screen components discussed herein.

Catheter procedure system 100 also includes an imaging system 104 located within lab unit 106. Imaging system 104 may be any medical imaging system that may be used in conjunction with a catheter based medical procedure (e.g., non-digital x-ray, digital x-ray, CT, MRI, ultrasound, etc.). In an exemplary embodiment, imaging system 104 is a digital x-ray imaging device that is in communication with workstation 116. In one embodiment, imaging system 104 may include a C-arm (not shown) that allows imaging system 104 to partially or completely rotate around patient 102 in order to obtain images at different angular positions relative to patient 102 (e.g., sagittal views, caudal views, anterior-posterior views, etc.).

Imaging system 104 may be configured to take x-ray images of the appropriate area of patient 102 during a particular procedure. For example, imaging system 104 may be configured to take one or more x-ray images of the heart to diagnose a heart condition. Imaging system 104 may also be configured to take one or more x-ray images during a catheter based medical procedure (e.g., real time images) to assist the user of workstation 116 to properly position a guide wire, guide catheter, stent, etc. during the procedure. The image or images may be displayed on first monitor 120 and/or second monitor 122. In particular, images may be displayed on first monitor 120 and/or second monitor 122 to allow the user to, for example, accurately move a guide catheter into the proper position.

In addition, a user of workstation 116 may be able to control the angular position of imaging system 104 relative to the patient to obtain and display various views of the patient's heart on first monitor 120 and/or second monitor 122. Displaying different views at different portions of the procedure may aid the user of workstation 116 to properly move and position the percutaneous interventional devices within the 3D geometry of the patient's heart. In an embodiment, imaging system 104 may be a 2D imaging system. In another embodiment, imaging system 104 may be any 3D imaging modality such as an x-ray based computed tomography (CT) imaging device, a magnetic resonance imaging device, a 3D ultrasound imaging device, etc. In this embodiment, the image of the patient's heart that is displayed during the procedure may be a 3D image. In addition, controls 118 may also be configured to allow the user positioned at workstation 116 to control various functions of imaging system 104 (e.g., image capture, magnification, collimation, c-arm positioning, etc.).

Figure 2:
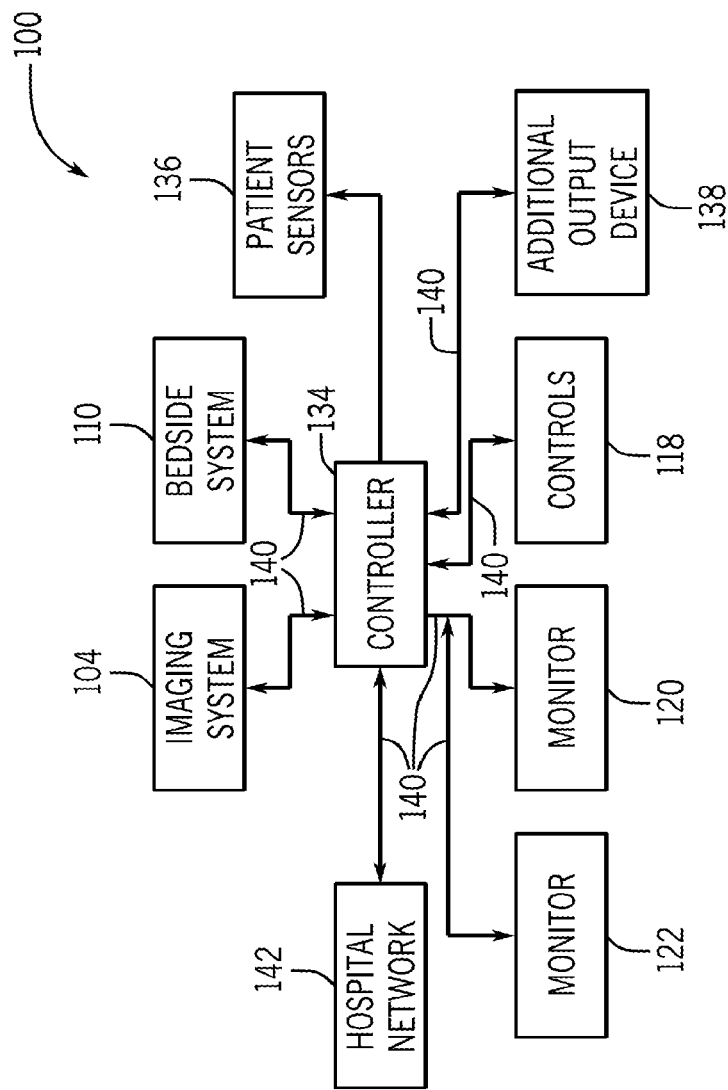
FIG. 2 is a schematic block diagram of a catheter procedure system in accordance with an embodiment.

Referring to FIG. 2, a block diagram of catheter procedure system 100 is shown according to an exemplary embodiment. Catheter procedure system 100 may include a control system, shown as controller 134. Controller 134 may be part of workstation 116. Controller 134 may generally be an electronic control unit suitable to provide catheter procedure system 100 with the various functionalities described herein. For example, controller 134 may be an embedded system, a dedicated circuit, a general purpose system programed with the functionality described herein, etc. Controller 134 is in communication with one or more bedside systems 110, controls 118, monitors 120 and 122, imaging system 104 and patient sensors 136 (e.g., electrocardiogram ("ECG") devices, electroencephalogram ("EEG") devices, blood pressure monitors, temperature monitors, heart rate monitors, respiratory monitors, etc.). In various embodiments, controller 134 is configured to generate control signals based on the user's interaction with controls 118 and/or based upon information accessible to controller 134 such that a medical procedure may be performed using catheter procedure system 100. In addition, controller 134 may be in communication with a hospital data management system or hospital network 142 and one or more additional output devices 138 (e.g., printer, disk drive, cd/dvd writer, etc.).

Communication between the various components of catheter procedure system 100 may be accomplished via communication links 140. Communication links 140 may be dedicated wires or wireless connections. Communication links 140 may also represent communication over a network. Catheter procedure system 100 may be connected or configured to include any other systems and/or devices not explicitly shown. For example, catheter procedure system 100 may include IVUS systems, image processing engines, data storage and archive systems, automatic balloon and/or stent inflation systems, medicine injection systems, medicine tracking and/or logging systems, user logs, encryption systems, systems to restrict access or use of catheter procedure system 100, etc.

Figure 3:
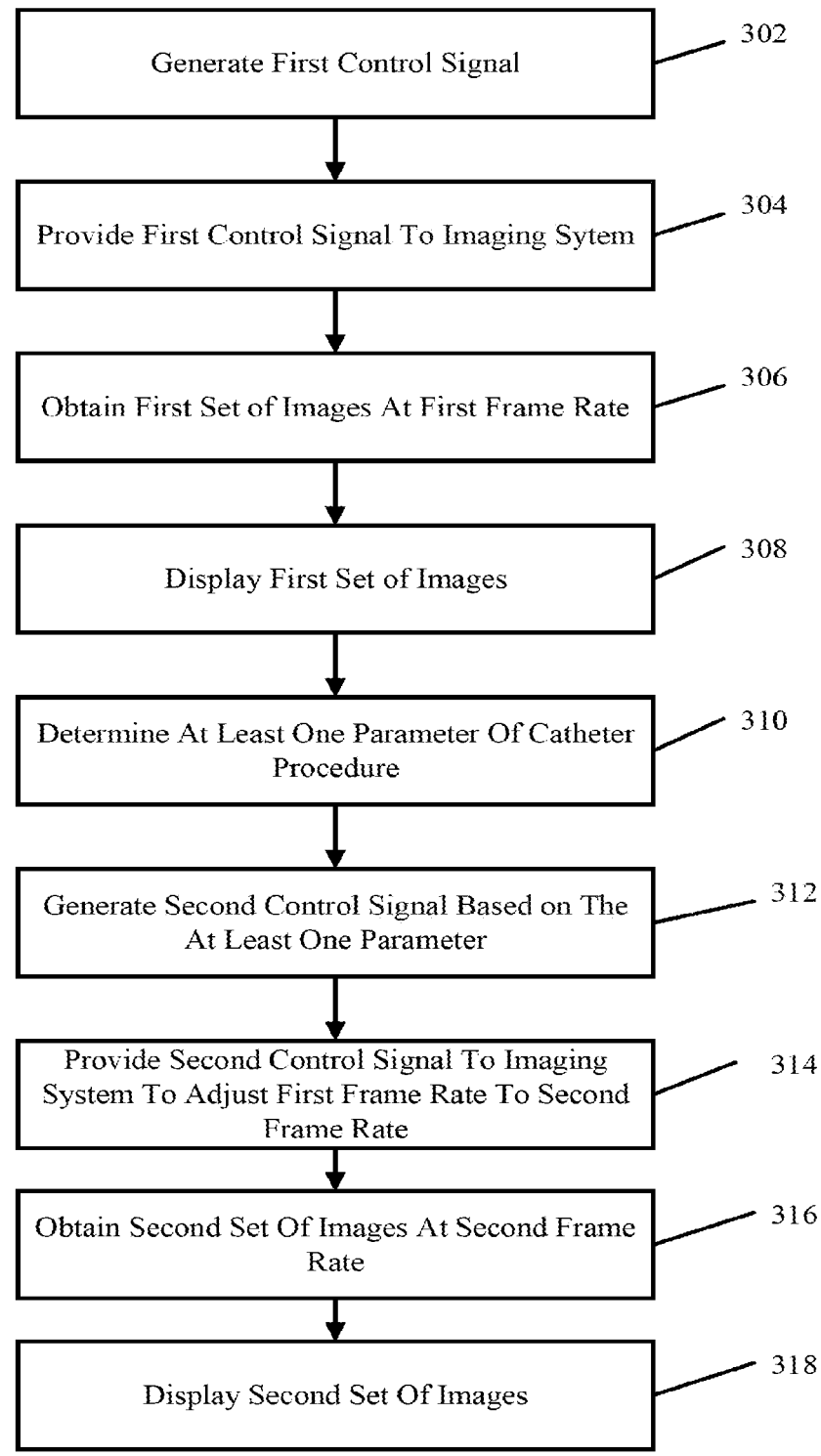
FIG. 3 illustrates a method for controlling x-ray frame rate of an imaging system for a catheter procedure system in accordance with an embodiment.

As mentioned above, the controller 134 is in communication with the imaging system 104 and controller 134 may be used to control the imaging system 104. In one embodiment, controller 134 is configured to adjust the frame rate (e.g., x-ray frame rate) utilized by imaging system 104 based on various parameters or states of the catheter procedure being performed using the catheter procedure system 100. FIG. 3 illustrates a method for controlling x-ray frame rate of an imaging system for a catheter procedure system in accordance with an embodiment. At block 302, controller 134 (shown in FIG. 2) generates a first control signal for the imaging system 104 (shown in FIGS. 1 and 2). The first control signal indicates a first frame rate (e.g., frames per second) for image acquisition by the imaging system 104. In one embodiment, the first frame rate is a predetermined frame rate, for example, a standard frame rate for use unless, as described further below, the characteristics of the catheter procedure indicate a state where an alternative frame rate (e.g., lower or higher) may be used for image acquisition. In another embodiment, as discussed further below, the first frame rate is selected based on one or more parameters of the catheter procedure. At block 304, controller 134 provides the first control signal to the imaging system 104 and, at block 306, the imaging system obtains a first set of images at the first frame rate. At block 308, the first set of images may be displayed, according to an embodiment, using, for example, a display 120 or 122 of the catheter procedure system.

At block 310, at least one parameter of the catheter procedure is determined and, at block 312, a second control signal is generated by controller 134 based on the at least one parameter to indicate a second frame rate for image acquisition by the imaging system 104. Accordingly, the frame rate utilized by the imaging system may be adjusted automatically based on the different states of the catheter procedure. In one embodiment, the parameter of the catheter procedure is the speed of a percutaneous device being advanced through the vasculature of the patient by the catheter procedure system. For example, the percutaneous device may be a guide wire and the parameter is the speed of the distal end or tip of the guide wire as it is moved within the patient. In one embodiment, if the speed of the percutaneous device is slower than a predetermined threshold, the second frame rate is selected to be a higher frame rate than the first frame rate or the same frame rate as the first frame rate. If the speed of the percutaneous device is faster than the predetermined threshold, the second frame is selected to be a lower frame rate than the first frame rate or the same frame rate as the first frame rate.

In another embodiment, the parameter of the catheter procedure is the magnification level selected by a user (e.g., using user interface 126) for viewing a region of interest of the images generated by the imaging system. If the magnification level is increased to "zoom-in" on a region of interest, e.g., the magnification level is selected to be greater than a predetermined magnification threshold, the second frame rate may be selected to be a higher frame rate than the first frame rate. If the magnification level is reduced to the predetermined magnification threshold or below the predetermined magnification threshold to "zoom-out", the second frame rate may be selected to be a lower or reduced frame rate than the first frame rate.

Figure 4:
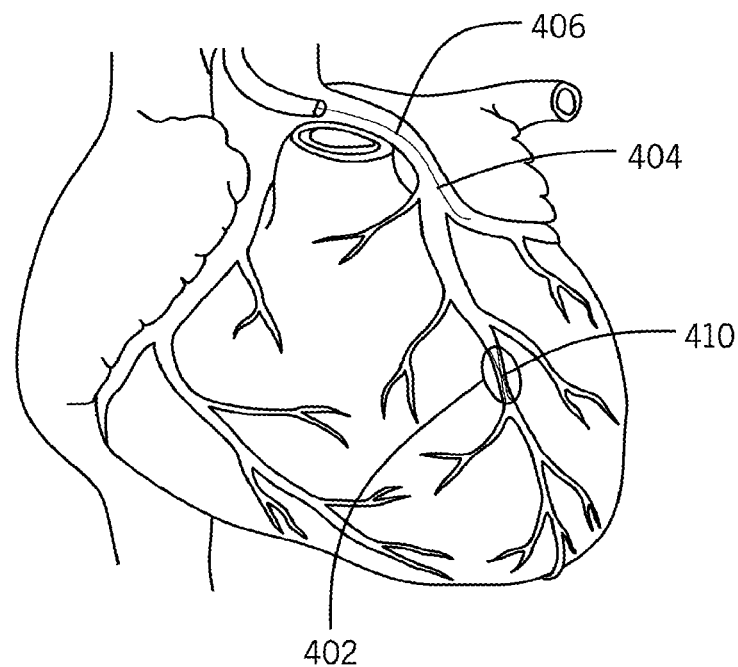
FIG. 4 illustrates an exemplary path of a percutaneous device to a lesion in accordance with an embodiment.
Figure 5:
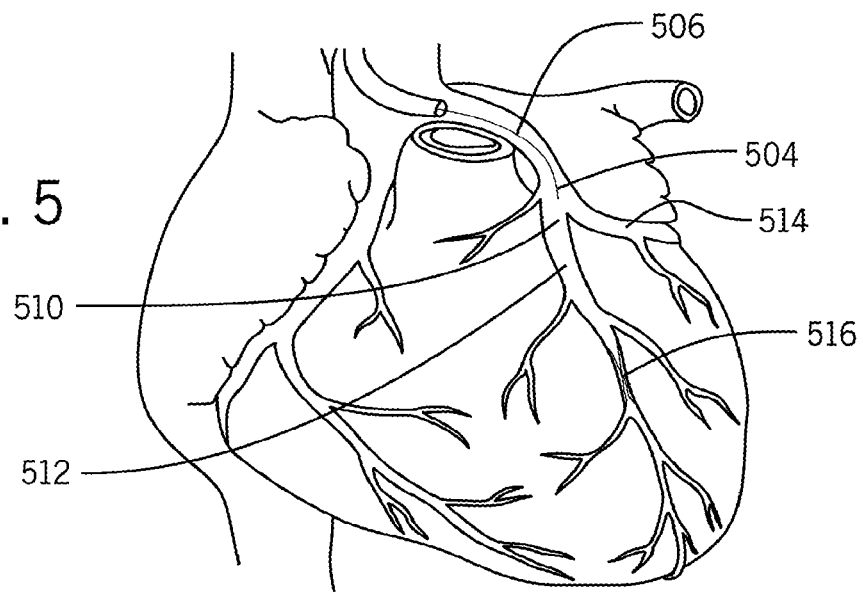
FIG. 5 illustrates an exemplary path of a percutaneous device to a lesion in accordance with an embodiment.

In another embodiment, the parameter is the location of a percutaneous device (or a selected portion of the percutaneous device) positioned within or being advanced through the vasculature by the catheter procedure system. The location of the percutaneous device may be determined using, for example, the images obtained by the imaging system either by a user or automatically using the controller of the catheter procedure system. In one embodiment, the parameter is the location of the percutaneous device (or a selected portion of the percutaneous device) in relation to a region of interest (i.e., the proximity to or a distance between the percutaneous device and the region of interest) such as a lesion. For example, a region 402 having a predetermined distance before and after a lesion 410 may be identified as shown in FIG. 4. When the distal end 404 of, for example, a guide wire 406 is within the region 402, the second frame rate may be selected to be higher than the first frame rate. In another embodiment, the parameter is the location of the percutaneous device (or a selected portion of the percutaneous device) in relation to the geometry of the vasculature such as, for example, the width of the lumen proximate to a distal end of the percutaneous device or the proximity of a distal end of the percutaneous device to a juncture in the vasculature. If the width of the vasculature proximate a distal end of, for example, a guide wire is greater than a predetermined width, then the second frame rate may be selected to be lower than the first frame rate. If the width of the vasculature proximate a distal end of the guide wire is led than a predetermined width, then the second frame rate may be selected to be the same as or higher than the first frame rate. In another example, a path to a lesion 516 may pass through one or more junction points or junctures 510 in the coronary anatomy as shown in FIG. 5. At juncture 510, the distal end 504 of a percutaneous device, for example, a guide wire 506, may be advanced down either a first lumen 512 or a second lumen 514. The distal end 504 of the guide wire 506 should be advanced through the proper lumen to reach the desired location, for example, lesion 516. The location of the distal end 504 of the guide wire 506 and the juncture 510 may be determined using, for example, the images obtained by the imaging system either by a user or automatically using the controller of the catheter procedure system. If the distal end 504 is located proximate to (e.g., at a predetermined distance from) the juncture 510, the second frame rate may be selected to be higher than the first frame rate. If the distal end 504 is not located within a predetermined distance from the juncture 510, the second frame rate may be selected to be the same as or lower than the first frame rate.

Figure 6:
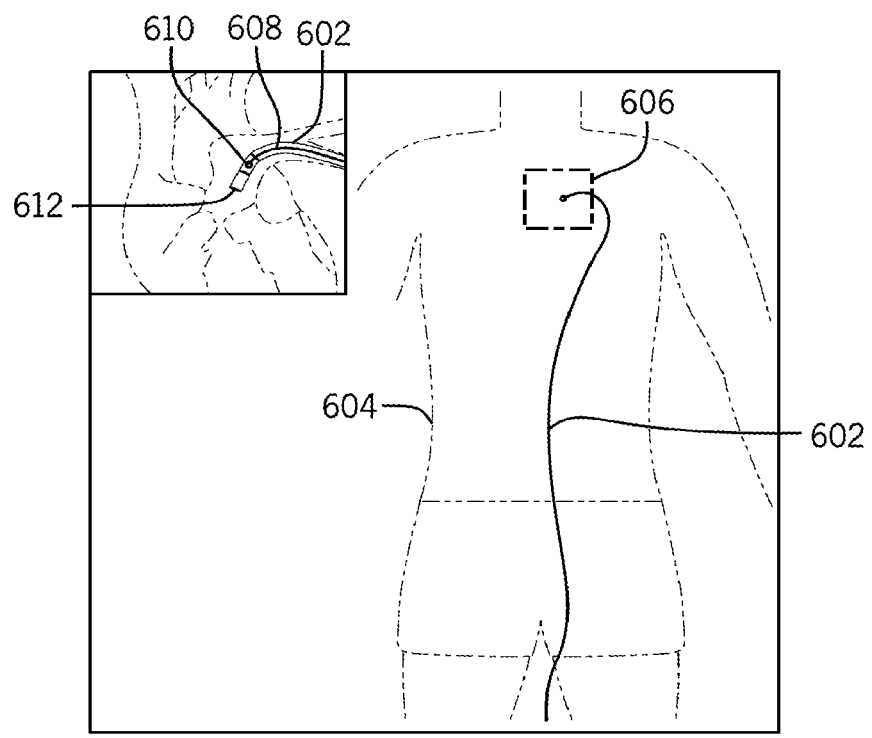
FIG. 6 is a schematic of the placement of a guide catheter and a guide wire in accordance with an embodiment.

In another embodiment, the parameter of the catheter procedure is the location of a first percutaneous device in relation to a second percutaneous device. For example, the location of a guide wire within a guide catheter as the guide wire is navigated towards a lesion or other region of interest. FIG. 6 is a schematic of the placement of a guide catheter and a guide wire in the vasculature of a patient in accordance with an embodiment. In FIG. 6, a guide catheter 602 has been fed into the torso 604 of a patient to reach the cardiac region 606. Within the guide catheter 602 is a guide wire 608 which distal end or tip 610 has not yet passed out of the distal end 612 of the guide catheter 602. The images obtained by the imaging system may be used to identify the location of the guide wire 608 within the guide catheter 602 and monitor the progress of the guide wire 6087 as it passes through the guide catheter 602. If the guide wire 608 is located within the guide catheter and the distal end of 610 of the guide wire 608 has not yet passed out of the guide catheter 602, the second frame rate may be selected to be lower than the first frame rate.

In another embodiment, the parameter of the catheter procedure is a comparison of successive images obtained by the imaging system to identify, for example, movement of the vasculature (e.g., a beating heart) or if the percutaneous device is not moving or idle. If a selected portion of the percutaneous device (e.g., the distal end of a guide wire) is located within a region of moving vasculature, the second frame rate may be selected to be higher than the first frame rate. If the selected portion of the percutaneous device is not located within a region of moving vasculature, the second frame rate may be selected to be the same as or lower than the first frame rate. If the percutaneous device is idle, the second frame rate may be selected to be lower than the first frame rate.

Once the second frame rate is selected and the second control signal has been generated, the controller 134 provides the second control signal to the imaging system at block 314 to adjust the first frame rate to the second frame rate. At block 316, the imaging system obtains a second set of images at the second frame rate. At block 318, the second set of images may be displayed, according to an embodiment, using, for example, a display 120 or 122 of the catheter procedure system. One or more of the parameters discussed above may be used to adjust the frame rate as the catheter procedure is performed and progresses through different states of the procedure (e.g., the advancement and location of the percutaneous device within the vasculature). By identifying when the frame rate may be reduced, the x-ray exposure or dose during the procedure may be reduced.

Computer-executable instructions for controlling x-ray frame rate of an imaging system for a catheter procedure system according to the above-described method may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which can be used to store the desired instructions and which may be accessed by system 10 (shown in FIG. 1), including by internet or other computer network form of access.

This written description used examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

What is claimed is:

1. A method for controlling an x-ray frame rate of an imaging system for a catheter procedure system, the method comprising:
    determining, based on a first set of images obtained from the imaging system at a first frame rate, that an end of a first percutaneous device is located within a second percutaneous device;

in response to determining that the end of the first percutaneous device is located within the second percutaneous device, changing the first frame rate to a second frame rate;
and
displaying a second set of images obtained from the imaging system at the second frame rate.

2. The method according to claim 1, wherein the second frame rate is lower than the first frame rate.

3. The method according to claim 1, further comprising determining a magnification level of at least one image in the first set of images,
wherein the first frame rate is changed to the second frame rate in response to determining that the end of the first percutaneous device is located within the second percutaneous device and that the magnification level exceeds a threshold level.

4. The method according to claim 3, wherein the second frame rate is lower than the first frame rate.

5. The method according to claim 1, further comprising determining motion of a region of a vasculature,
wherein the first frame rate is changed to the second frame rate in response to determining that the end of the first percutaneous device is located within the second percutaneous device and that the motion of the region of the vasculature exceeds a threshold level.

6. The method according to claim 5, further comprising determining a second position of the end of the first percutaneous device in relation to a geometry of the vasculature,
wherein the first frame rate is changed to the second frame rate in response to determining that the end of the first percutaneous device is located within the second percutaneous device, that the motion of the region of the vasculature exceeds the threshold level, and that the second position of the end of the first percutaneous device is in a particular relation to the geometry of the vasculature.

7. The method according to claim 1, further comprising determining a second position of the end of the first percutaneous device in relation to a geometry of a vasculature,
wherein the first frame rate is changed to the second frame rate in response to determining that the end of the first percutaneous device is located within the second percutaneous device and that the second position of the end of the first percutaneous device is in a particular relation to the geometry of the vasculature.

8. The method according to claim 1, wherein the step of changing the first frame rate to the second frame rate comprises sending a signal to the imaging system to change the first frame rate to the second frame rate.

9. A catheter procedure system comprising:
at least one drive mechanism coupled to at least one of a first percutaneous device and a second percutaneous device; and
a controller programmed to:
generate a first control signal that indicates a first frame rate;
determine at least one parameter of a catheter procedure performed by the catheter procedure system;
generate a second control signal based on the at least one parameter of the catheter procedure, the second control signal indicating a second frame rate; and
adjust the first frame rate to the second frame rate, and
wherein the at least one parameter of the catheter procedure is an indication of whether an end of the first percutaneous device is located within the second percutaneous device.

10. The catheter procedure system according to claim 9, wherein the second frame rate is lower than the first frame rate.

11. The catheter procedure system according to claim 10, wherein the at least one parameter further includes a magnification level.

12. The catheter procedure system according to claim 11, wherein the at least one parameter further includes motion of a region of a vasculature.

13. The catheter procedure system according to claim 9, wherein the at least one parameter further includes a magnification level.

14. The catheter procedure system according to claim 13, wherein the at least one parameter further includes a second position of the end of the first percutaneous device in relation to a geometry of a vasculature.

15. The catheter procedure system according to claim 9, wherein the at least one parameter further includes motion of a region of a vasculature.

16. The catheter procedure system of claim 8, wherein the step of adjusting the first frame rate to the second frame rate comprises providing the second control signal to an imaging system to adjust the first frame rate to the second frame rate.

17. A method for controlling an imaging system for a catheter procedure system, the method comprising:
receiving at least one image from the imaging system, the at least one image acquired at a first frame rate;
determining, based on the at least one received image, that an end of a first percutaneous device is located within a second percutaneous device; and
providing a control signal to the imaging system to adjust the first frame rate to a second frame rate in response to determining that the end of the first percutaneous device is located within the second percutaneous device.

18. The method according to claim 17, wherein the second frame rate is lower than the first frame rate.

19. The method according to claim 18, further comprising:
determining a magnification level of the at least one received image,
wherein adjustment to the second frame rate is based on the magnification level.

20. The method according to claim 19, further comprising:
determining a second position of the end of the first percutaneous device in relation to a geometry of a vasculature,
wherein adjustment to the second frame rate is based on the determined second position.

21. The method according to claim 20, further comprising:
determining motion of a region of the vasculature,
wherein adjustment to the second frame rate is based on the determined motion.

22. The method according to claim 17, further comprising:
determining a magnification level of the at least one received image,
wherein adjustment to the second frame rate is based on the magnification level.

* * * * *